United States Patent
Hall et al.

(10) Patent No.: US 6,253,214 B1
(45) Date of Patent: *Jun. 26, 2001

(54) ULTRASOUND IMAGE INFORMATION ARCHIVING SYSTEM

(75) Inventors: Fred M. Hall, Ann Arbor, MI (US); Gerard A. Hranek, Sunnyvale, CA (US); Lloyd B. Kreuzer, Menlo Park, CA (US); Lawrence T. McNary, San Jose, CA (US); Mary Jeanne Rabold, San Carlos, CA (US); David A. Rock, Saline; Rex A. Timbs, Ipsalanti, both of MI (US)

(73) Assignee: Acuson Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/846,251

(22) Filed: Apr. 30, 1997

(51) Int. Cl.[7] ........................................ G06F 9/00
(52) U.S. Cl. ................... 707/204; 707/1; 707/3
(58) Field of Search .......................... 707/1–206

(56) References Cited

U.S. PATENT DOCUMENTS 4,958,283 * 9/1990 Tawara et al. ................. 382/131
5,715,823 * 2/1998 Wood et al. .................... 600/437

* cited by examiner

Primary Examiner—Thomas G. Black
Assistant Examiner—John G. Mills
(74) Attorney, Agent, or Firm—Brinks Hofer Gilson & Lione

(57) ABSTRACT

An ultrasound image information archiving system is provided for storing a reference copy of ultrasound image information. The system comprises a primary storage device, a secondary storage device, and control means for retrieving ultrasound image information, creating a reference copy of the ultrasound image information, and storing the reference copy in the secondary storage device. The system can be used in a method for storing a reference copy of ultrasound image information in which ultrasound image information is retrieved from a primary storage device and a reference copy of ultrasound image information is created and then stored in a secondary storage device. The system can also be used with a more general ultrasound image information archiving method.

18 Claims, 3 Drawing Sheets

Microfiche Appendix Included
(1 Microfiche, 20 Pages)

```
RETRIEVE ULTRASOUND IMAGE INFORMATION
                │
                │ 410
                ▼
      CREATE A REFERENCE COPY
      OF THE IMAGE INFORMATION      420
                │
                ▼
      STORE THE REFERENCE COPY IN    430
      THE SECONDARY STORAGE DEVICE
```

```
RETRIEVE THE ULTRASOUND IMAGE INFORMATION
                │ 510
                ▼
   STORE A COPY OF THE ULTRASOUND IMAGE
   INFORMATION IN THE ARCHIVE STORAGE DEVICE
                │ 520
                ▼
   UPDATE THE DATABASE STORAGE DEVICE TO INDICATE
   THAT THE IMAGE INFORMATION WAS ARCHIVED
                │ 530
                ▼
   CREATE A REFERENCE COPY OF THE
   ULTRASOUND IMAGE INFORMATION
                │ 540
                ▼
   STORE THE REFERENCE COPY IN THE
   SECONDARY STORAGE DEVICE
                │ 550
                ▼
   UPDATE THE DATABASE STORAGE DEVICE
   TO INDICATE THAT THE REFERENCE COPY WAS
   STORED IN THE SECONDARY STORAGE DEVICE
         560              │ 570
                ▼
   DELETE THE ULTRASOUND IMAGE INFORMATION
   IN THE PRIMARY STORAGE DEVICE
```

ULTRASOUND IMAGE INFORMATION ARCHIVING SYSTEM

MICROFICHE APPENDIX

This application includes one microfiche appendix containing 20 frames.

BACKGROUND OF THE INVENTION

When an ultrasound imaging system is connected into a diagnostic medical imaging network, ultrasound image information captured at the imaging system can be stored for future reference. Several systems and methods have been used to store such information. For example, image information has been archived onto a removable storage medium. After the information is archived, the storage medium is removed from a storage device and placed in a media library for safekeeping. To reference the image information, a user retrieves the medium from the library and places it in the storage device. As another example, image information has been printed on film media and manually stored in file folders. A user must retrieve the hard copy from the file folders to reference the image information.

There are several problems associated with these systems and methods. Manually retrieving information from a media library or a file folder is time consuming. There is also a risk that the storage medium or film will be lost or damaged. In addition, because ultrasound images are typically transmitted and stored as full-size images, network efficiency and storage density are reduced.

There is, therefore, a need for a system and method for storing reference copies of ultrasound image information that will overcome the problems described above.

SUMMARY OF THE INVENTION

The present invention is directed to an on-line storage system and method for storing reference copies of ultrasound image information.

According to a first aspect of this invention, an on-line high-density image storage system is provided for storing a reference copy of ultrasound image information. This system comprises a primary storage device, a secondary storage device, and control means for retrieving ultrasound image information, creating a reference copy of the ultrasound image information, and storing the reference copy in the secondary storage device.

According to a second aspect of this invention, a method for storing a reference copy of ultrasound image information is provided comprising the steps of retrieving ultrasound image information, creating a reference copy of the ultrasound image information, and storing the reference copy in the secondary storage device.

According to a third aspect of this invention, a method for archiving ultrasound image information is provided comprising the steps of retrieving ultrasound image information from a primary storage device, storing the ultrasound image information in an archive storage device, updating a database to indicate that the ultrasound image information was stored in the archive storage device, creating a reference copy of the ultrasound image information, storing the reference copy in a secondary storage device, updating a database to indicate that the reference copy was stored in the secondary storage device, and deleting the ultrasound image information from the primary storage device.

The preferred embodiments of the invention will now be described with reference to the attached drawings.

BRIEF DESCRIPTION OF THE DRAWINGS

FIG. 3 is a flow chart of a method for storing a reference copy of ultrasound image information in a secondary storage device of a second preferred embodiment.

FIG. 4 is a flow chart of a backup procedure used in an alternative to the second preferred embodiment.

DETAILED DESCRIPTION OF THE PRESENTLY PREFERRED EMBODIMENTS

FIRST PREFERRED EMBODIMENT

Figure 1:
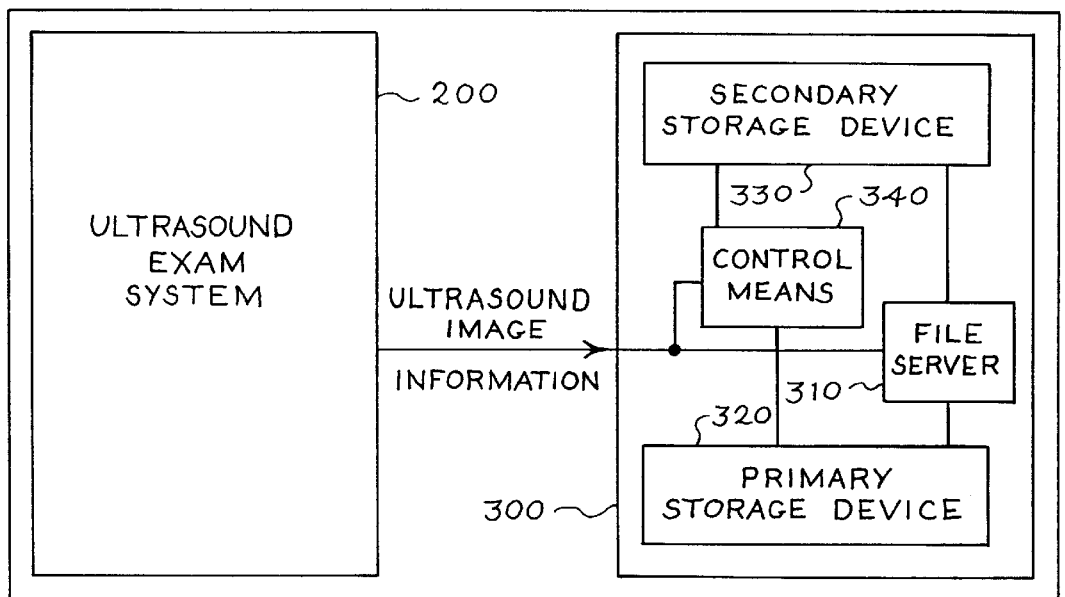
FIG. 1 is a block diagram of a diagnostic medical imaging network of a first preferred embodiment.

Turning now to the drawings, FIG. 1 shows a diagnostic medical imaging network 100 of a first preferred embodiment. The network 100 includes an ultrasound exam system 200 that is coupled to and responsive to an on-line high-density storage system 300, providing it with ultrasound image information. As used herein, the term "ultrasound image information" can include, but is not limited to, ultrasound images (which can include full- and reduced-size images) and related patient data (such as patient demographics and image-calculation data). Also as used herein, "coupled to" can mean directly coupled to or indirectly coupled through one or more components. Similarly, "responsive to" can mean directly responsive to or indirectly responsive through one or more components.

In the on-line high-density storage system 300, a file server 310, which is responsive to the ultrasound exam system 200, couples to a primary storage device 320 and a secondary storage device 330. Also present in this system 300 is control means 340 for retrieving ultrasound image information, creating a reference copy of the ultrasound image information, and storing the reference copy in the secondary storage device 330, as will be described in more detail below.

The control means 340 is responsive to the ultrasound exam system 200 and coupled to the primary storage device 320 and the secondary storage device 330. It is important to note that the control means may be placed anywhere in the network 100. For example, the control means can be located in the file server 310 or in an archive server in the ultrasound exam system 200. Additionally, the different functions performed by the control means can be separated and performed in two or more locations in the network 100.

Generally, the on-line high-density storage system 300 receives ultrasound image information from the ultrasound exam system 200 for initial storage in the primary storage device 320 through the file server 310. At a designated time, a reference copy of the ultrasound image information stored in the primary storage device 320 is created and stored in the secondary storage device 330. The reference copy can be created in a way that allows image information to be stored in the secondary storage device 330 at a higher density than in the primary storage device 320.

By using the on-line high-density storage system 300, a large pool of image information is available for on-line reference. In this way, reference copies of image information are made easily accessible without the need to manually locate and mount removable storage media.

Figure 2:
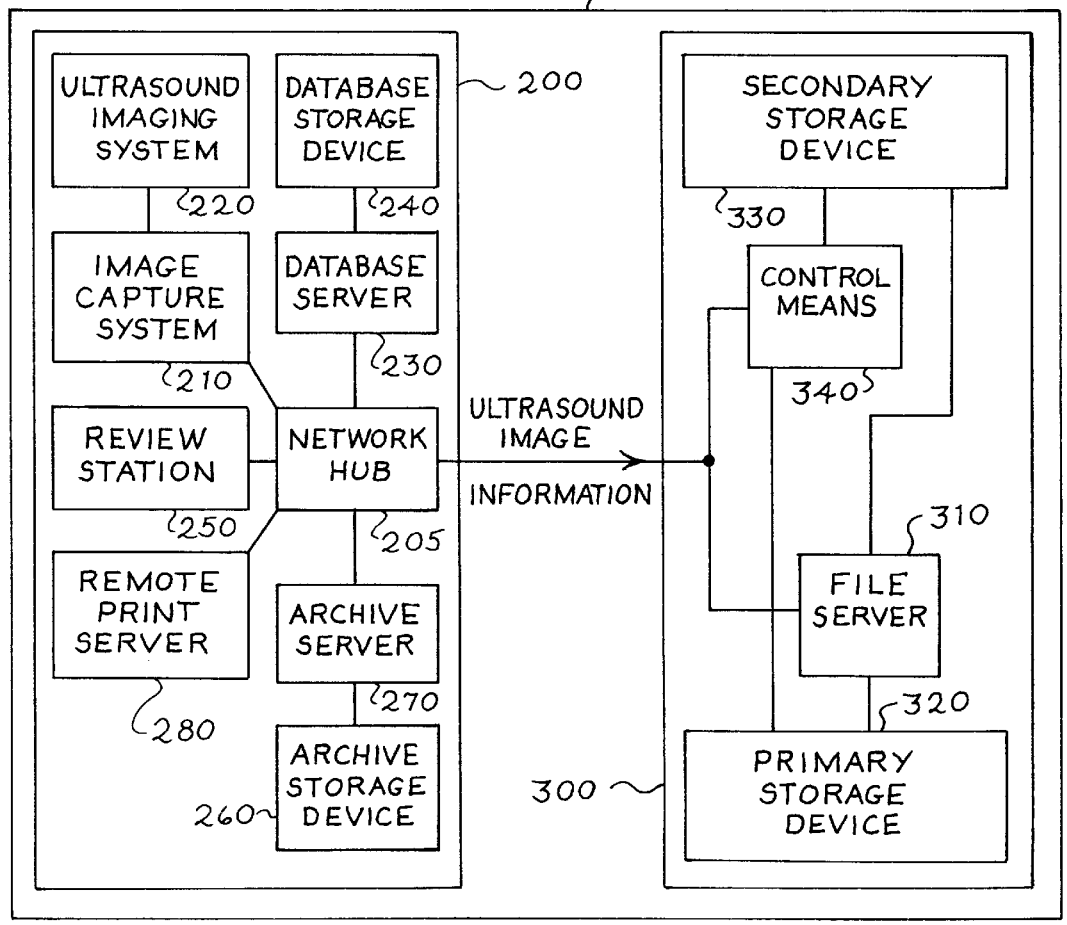
FIG. 2 is a block diagram showing components which can be used in the diagnostic medical imaging network of the first preferred embodiment.

FIG. 2 shows an example of a diagnostic medical imaging network 100 of a first preferred embodiment. Here, a network hub 205 couples an ultrasound image capture system 210, an archive server 270, a database server 230, a remote print server 280, and a review station 250. The capture system 210 is responsive to an ultrasound imaging system 220, the database server 230 is coupled to a database storage device 240, and the archive server 270 is coupled to an archive storage device 260.

It is important to note that FIG. 2 represents only one form of the ultrasound exam system 200 and that components may be removed or added to the system 200. For example, the archive server 270 can be coupled to a printer to print a hard copy of the image information. It is also important to note that while only one of each component is shown in this figure, multiple components can be used. For example, this network 100 can connect several ultrasound imaging systems and capture systems. The use of each of the shown components will be described briefly below.

An operator uses the ultrasound imaging system 220 to form an ultrasound image of a portion of a patient's body. The image capture system 210 sends this image, along with related patient data, through the network 100. Once on the network 100, the ultrasound image information can be viewed at the review station 250, printed at the remote print server 280, stored in the archive storage device 260 through the archive server 270, or stored in the primary 320 and secondary 330 storage devices in the on-line high-density storage system 300, as will be described in more detail below. The related patient data, as well as the location of the saved images, can be stored in the database storage device 240 through the database server 230.

To store more image information, it is often desired to store a reduced-size, rather than a full-size, image in the secondary storage device 330. The image capture system 210, for example, can create a reduced-size image of the full-size image it captures by using the well-known technique of pixel decimation.

To store more information in both the primary 320 and secondary 330 storage devices, as well as to increase network efficiency, the capture system 210 preferably compresses the ultrasound images (full-size, reduced-size, or both) before sending them through the network 100. Although any compression scheme can be used, it is preferred that a run length encoding scheme, an industry standard for compressing images, be used to reduce the size of the image (see Foley, J. D. and A. Van Dam. *Fundamentals of Interactive Computer Graphics*: Addison Wesley, 1984, pp. 498–499).

As mentioned above, ultrasound image information can include related patient data. Because patient data requires only a small amount of disk and network space, the related patient data is typically not compressed, although it can be if desired.

The second preferred embodiment, described below, provides a more detailed description of the method by which the reference copy is created and stored.

SECOND PREFERRED EMBODIMENT

The components and network of the first preferred embodiment are preferably used in a method for storing a reference copy of ultrasound image information in the secondary storage device 330. FIG. 3 shows the steps which comprise this method: retrieve ultrasound image information (block 410), create a reference copy of the image information (block 420), and store the reference copy in the secondary storage device 330 (block 430).

The reference copy is stored at any time designated by a user of the network. For example, a reference copy can automatically be stored at the end of an exam session or at the end of the day.

Retrieve Ultrasound Image Information (Block 410)

As shown in FIG. 3, the first step of the method is to retrieve the ultrasound image information (block 410). Any method of retrieving the information can be used. The ultrasound images preferably are retrieved from the primary storage device 320. Related patient data, if stored in the database storage device 240 instead of the primary storage device 320, can be retrieved from the database storage device 240.

Create a Reference Copy (Block 420)

The next step is to create a reference copy of the image information. A reference copy can be created to include the reduced-size image, the full-size image, the related patient data, or any combination of the above. That is, in some embodiments, the reference copy is an exact duplicate of the image information stored in the primary storage device 320 and the database storage device 240, if used to store image information. In other embodiments, the reference copy contains only a subset of the image information.

Store the Reference Copy (Block 430)

The third step is to store the reference copy in the secondary storage device 330. This step can comprise nothing more than saving the reference copy in the secondary storage device 330. This step, however, can also comprise the additional steps of establishing a storage location in the secondary storage device 330 and labeling each reference copy with an identifier, which can be used to locate the reference copy.

If there is not enough storage space available in the secondary storage device 330, a previously-stored reference copy can be deleted to provide the necessary storage space. While any reference copy can be deleted, it may be desired to delete the oldest one.

To ensure data safety, the secondary storage device 330 can have a level-five redundant-array-of-independent-disks configuration. As is well known in the art, this configuration stripes data and parity information across a plurality of disks. In this way, if one of the disks fails, the lost information can be easily reconstructed.

Advantages

The system and method described above offer advantages over prior-art systems and methods in terms of speed, convenience, and reduced storage cost per exam. Speed is increased due to the on-line availability of reference copies of ultrasound image information. Medical personnel no longer need to manually search for archive media and import image information into their medical systems in order to review images.

Convenience is also enhanced. If only the reduced-size image (with or without the related patient data) is stored, many months of exams can be stored on-line, resulting in reduced storage costs per exam.

Alternatives

Image Backup System

As mentioned above, the reference copy can be stored in the secondary storage device 330 at any designated time. The method described above can also be part of a larger image backup system, as illustrated in FIG. 4.

As with the method described above, the first step is to retrieve the ultrasound image information (block 510). This step is identical to the step of the above method. Next, a copy of the ultrasound image information is stored in the archive storage device 260 (block 520). To ensure data safety, the archive storage device 260 has a level-one redundant-array-of-independent-disks configuration to store the image information on two disk drives.

After the archive storage device 260 stores the image information, the database server 230 updates the database storage device 240 to indicate that the image information has been archived (block 530).

Next, a reference copy of the ultrasound image information is created (block 540) and stored in the secondary storage device 330 (block 550), as described in the above method. Then, the database server 230 updates the database storage device 240 to indicate that the reference copy was stored in the secondary storage device 330 (block 560). A record of the exam location in the secondary storage device 330 is made in the database storage device 240.

With the image information archived and a reference copy stored, the ultrasound image information in the primary storage device 320 is deleted (block 570) to provide space for storing future exams.

Viewing the Reference Copy

Once a reference copy is stored in the secondary storage device 330, it may be accessed through the network 100. Once accessed, the reference copy may be viewed at a number of places in the network 100. For example, the reference copy can be displayed on the review station 250 or printed to film media at the remote print server 280 or at a printer attached to the archive server 270, if present.

To view the reference copy, it must first be retrieved from the secondary storage device 330. The reference copy can then be decompressed if it was previously compressed. If the reference copy contains a reduced-size image, any suitable pixel interpolation technique can be used to smooth the image.

Storage Architecture

Figure 5:
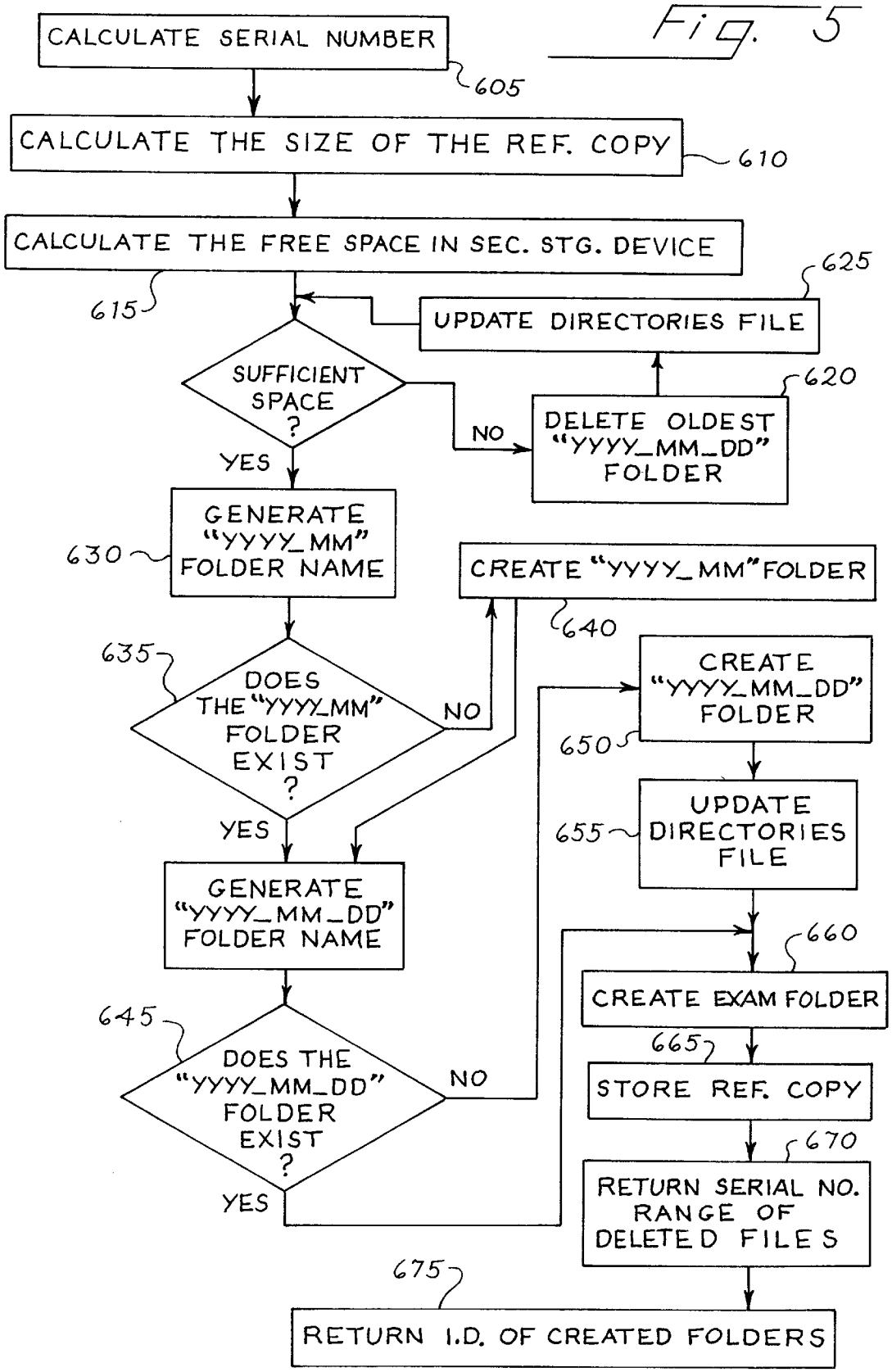
FIG. 5 is a flow chart of a storage technique which can be used in the second preferred embodiment.

As part of the step of storing the reference copy in the secondary storage device 330, a location in the secondary storage device 330 is preferably established. FIG. 5 shows one example of how this may be performed.

First, a serial number is calculated for the reference copy (block 605). The serial number can represent the number of seconds that have passed since a particular time and the time that the exam was performed, for example. Next, the size of the reference copy and the amount of free space available in the secondary storage device 330 are calculated (blocks 610 and 615). If there is insufficient space to store the reference copy, the oldest file folder is deleted (block 620), and a directory in the secondary storage device 330 containing a reference to all the folders is updated accordingly (block 625).

Next, a new file folder, labeled with the appropriate year and month, is created if it does not already exist (blocks 630, 635, 640). Within this folder, another folder, labeled with the appropriate day, is created, if it does not already exist (blocks 645 and 650). If a new folder is created, the directory is updated accordingly (block 655).

In this folder, an exam folder is created (block 660). The reference copy is stored in this folder or additional folders created therein (block 665). Additional reference copies are stored until there are none remaining. Finally, the serial number range of the deleted files and the identification number (i.e., the serial number) of the new folders that were created are returned (blocks 670 and 675) to the database storage device 240.

File Management

There may be instances in which the secondary storage device 330 contains reference copies that are not recorded in the database storage device 240. There may also be instances in which the database storage device 240 contains a record of a location in the secondary storage device 330 that does not contain a reference copy. In these situations, the reference copy or the record, respectively, is preferably deleted.

Best Mode

While pixel decimation can be used to reduce the full-size image to any desired size, it is preferred that the reduced-size image be a quarter-size image. A quarter-size image has sufficient image quality to be useful for reference, although perhaps not for diagnostic, purposes.

The above embodiments describe control means for retrieving ultrasound image information, creating a reference copy of the image information, and storing the reference copy in the secondary storage device 330. While this control means can be implemented with hardware, it is preferred that computer software be used to accomplish the functions of the control means. It is also preferred that the software reside in the component (e.g., the archive server 270) that controls the exam archiving process. A preferred software implementation is illustrated in the microfiche appendix attached hereto and made part of this application.

Preferably, the ultrasound image information is sent through the network and stored in three tracks. One track preferably contains the full-size ultrasound image, and another track preferably contains the quarter-size ultrasound image. It is preferred that these two tracks be in a Quicktime movie format. The third track preferably contains the related patient data tagged with a DICOM element, a standard information tag used in the medical industry.

As mentioned above, the ultrasound image information is sent through the network and stored in three tracks. To store more information, it is preferred only to store the quarter-size image and the related patient data in the secondary storage device 330. Because three tracks of information are sent everywhere else in the network 100, it is preferred to send three tracks to the secondary storage device 330. Instead of sending the full-size image on the third track, however, a single black full-size frame is sent. For each additional black frame, references to the previously-sent single black full-size frame are sent instead of resending the entire black frame. In this way, three tracks of information are sent without sacrificing much storage space.

The following example illustrates how using the above embodiments allow image information to be stored in the secondary storage device 330 at a higher density than in the primary storage device 320. Assume that the resolution of a full-size image is 640×480 and that the color depth is 24 bits. Also assume that there are 40 image frames per ultrasound examination and that the images are compressed to 0.28 of their original size. Finally, assume that the related patient data and the blackened, full-size ultrasound image require a negligible amount of storage space.

Accordingly, a full-size image would require 258,048 bytes (640*480*24*0.28=2,064,384 bits=258,048 bytes). A quarter-size image would require 64,512 bytes (258,048*0.25=64,512 bytes). With forty frames per exam, storing both the full- and quarter-size images in the primary storage device 320 would require 12.9 megabytes ((258,048+64,512)*40=12.9 megabytes). Storing an exam having only quarter-size images in the secondary storage device 330 requires 2.6 megabytes (64,512*40=2.6 megabytes).

As can be seen by this example, storing only the quarter-size images in the secondary storage device 330 allows a deeper repository of ultrasound image information for on-line reference, reducing the need for the user to handle long-term storage media.

The following is a description of the preferred components used in the ultrasound exam network 100. The ultrasound imaging system 220 is preferably an XP, Aspen, or Sequoia system made by Acuson Corp., and the capture system 210 is preferably a QV100 system, also made by Acuson Corp. The capture system 210 comprises a Quadra 650 motherboard from Apple Computers, a 3.5" magneto-optical disk drive made by Fujitsu, a Photopro PCB image compressor, and a MXRGB frame grabber, both manufactured by RastorOps. It is important to note that the capture system can be made an integral part of the ultrasound imaging system.

The review station 250 preferably comprises a model 8500 computer from Apple Computers, a 3.5" magneto-optical disk drive made by Fujitsu, a XClaim video driver PCB from ATI, and a 20" monitor, preferably model number EO3 from Sony Corp. The remote print server 280 preferably comprises a model 7100 computer from Apple Computers, a 14" monitor from Tatung, a 3.5" magneto-optical disk drive made by Fujitsu, and a PCB print driver from either 3M or SuperMac.

The network hub 205 preferably is a 24 port 10BaseT ethernet hub from Allied Telesyn. The hub 205 links the components of the network 100 via a STAR network topology. Token rings and common busses, for example, can also be used to link the components. The archive server 270 preferably comprises a model 8100 computer from Apple Computers, a 3.5" magneto-optical disk drive made by Fujitsu, a 14" monitor from Tatung, and a PCB printer driver from either 3M or SuperMac.

The archive storage device 260 is preferably a 2.6 gigabyte 5.25" magnetooptical drive manufactured by Hewlett Packard. The primary storage device 320 is preferably a 8.4 gigabyte diskpack manufactured by SUN and preferably has a level-one redundant-array-of-independent-disks configuration, a well-known storage configuration in which identical information is stored on two disk drives.

The secondary storage device 330 preferably comprises a six-bay diskpack with five 4.2 gigabyte hard drives from SUN. The file server 310 is preferably a 110 MHz Sparc 5 system from SUN.

The database server 230 is preferably a model 6100 computer from Apple Computers with a 28.8 baud FAX-modem from Supra. The data base storage device 240 preferably comprises a pair of 1 gigabyte hard drives from Seagate and preferably has a level-one redundant-array-of-independent-disks configuration.

When the above components are used to store quarter-size ultrasound images, roughly 6–12 months worth of exams for the average lab can be stored on-line. It is important to note, however, that other components can be used. For example, tape-base media, such as digital audio tapes, and a magneto-optical jukebox with a robotic disk selector can be used as storage devices.

It is intended that the foregoing detailed description be understood as an illustration of selected forms that the invention can take and not as a definition of the invention. It is only the following claims, including all equivalents, which are intended to define the scope of this invention.

What is claimed is:

1. A method for providing a reduced-size version of a full-size version of an ultrasound image for on-line reference in a diagnostic medical imaging network, the method comprising:
   (a) creating an ultrasound image with an ultrasound imaging system;
   (b) storing a full-size version of the ultrasound image and a reduced-size version of the full-size version of the ultrasound image in a primary storage device coupled with the ultrasound imaging system;
   (c) storing a reduced-size version of the full-size version of the ultrasound image in a secondary storage device coupled with the primary storage device, whereby the secondary storage device stores ultrasound images at a higher density than the primary storage device, wherein said storing comprises providing storage space in the secondary storage device by deleting a previously-stored reduced-size version of an ultrasound image; and
   (d) deleting the previously-stored full-size version of the ultrasound image in the primary storage device, whereby the reduced-size version of the full-size version of the ultrasound image stored in the secondary storage device is available for on-line reference after the previously-stored full-size version of the ultrasound image is deleted from the primary storage device.

2. The invention of claim 1, wherein the reduced-size version of the full-size version of the ultrasound image comprises a quarter-size version of the full-size version of the ultrasound image.

3. The invention of claim 1, wherein (c) comprises establishing a storage location in the secondary storage device.

4. The invention of claim 1 further comprising:
   retrieving related patient data from a database storage device; and
   storing the related patient data in the secondary storage device.

5. The invention of claim 1, wherein the secondary storage device comprises a level-five redundant-array-of-independent-disks configuration.

6. The invention of claim 1, wherein the secondary storage device comprises a hard drive.

7. The invention of claim 1, wherein the full-size version of the ultrasound image stored in the primary storage device is of higher image quality than the reduced-size version stored in the secondary storage device.

8. The invention of claim 1 further comprising storing the full-size version of the ultrasound image in an archive storage device.

9. The invention of claim 8, further comprising updating a database to indicate that the full-size version of the ultrasound image was stored in the archive storage device.

10. The invention of claim 8, further comprising updating a database to indicate that the reduced-size version of the ultrasound image was stored in the secondary storage device.

11. A method for providing a reduced-size version of a full-size version of an ultrasound image for on-line reference, the method comprising:
    (a) storing a full-size version of an ultrasound image and a reduced-size version of the full-size version of the ultrasound image in a first on-line storage device;
    (b) storing the reduced-size version of the full-size version of the ultrasound image in a second on-line storage device; and
    (c) deleting the nervously-stored full-size version of the ultrasound image and the previously-stored reduced-size version of the full-size version of the ultrasound image from the first on-line storage device;
    whereby the reduced-size version of the full-size version of the ultrasound image is available for on-line reference after the previously-stored full-size version of the ultrasound image and the previously-stored reduced-size version of the full-size version of the ultrasound image are deleted from the first on-line storage device.

12. The invention of claim 11, wherein the reduced-size version of the full-size version of the ultrasound image comprises a quarter-size version of the full-size version of the ultrasound image.

13. The invention of claim 11, wherein the full-size version of the ultrasound image stored in the first on-line storage device is of higher image quality than the reduced-size version stored in the second on-line storage device.

14. The invention of claim 11 further comprising repeating acts (a)–(c), whereby the second on-line storage device stores reduced-size versions of the full-size versions of the ultrasound images at a higher density than the first on-line storage device stores full-size versions of the ultrasound images.

15. A method for providing a reduced-size version of a full-size version of an ultrasound image for on-line reference, the method comprising:

(a) storing a full-size version of an ultrasound image and a reduced-size version of the full-size version of the ultrasound image in a first on-line storage device;

(b) archiving the full-size version of the ultrasound image in an archive storage device;

(c) storing the reduced-size version of the fill-size version of the ultrasound image in a second on-line storage device; and (d) deleting the previously-stored fill-size version of the ultrasound image and the previously-stored reduced-size version of the full-size version of the ultrasound image from the first on-line storage device;

whereby the reduced-size version of the full-size version of the ultrasound image is available for on-line reference after the full-size version of the ultrasound image is archived and after the previously-stored full-size version of the ultrasound image and the previously-stored reduced-size version of the full-size version of the ultrasound image are deleted from the first on-line storage device.

16. The invention of claim 15, wherein the reduced-size version of the full-size version of the ultrasound image comprises a quarter-size version of the full-size version of the ultrasound image.

17. The invention of claim 15, wherein the full-size version of the ultrasound image stored in the first on-line storage device is of higher image quality than the reduced-size version stored in the second on-line storage device.

18. The invention of claim 15 further comprising repeating acts (a)–(d), whereby the second on-line storage device stores reduced-size versions of the full-size versions of the ultrasound images at a higher density than the first on-line storage device stores full-size versions of the ultrasound images.

* * * * *

UNITED STATES PATENT AND TRADEMARK OFFICE
CERTIFICATE OF CORRECTION

PATENT NO.    : 6,253,214 B1
DATED         : June 26, 2001
INVENTOR(S)   : Fred M. Hall et al.

It is certified that error appears in the above-identified patent and that said Letters Patent is hereby corrected as shown below:

<u>Title page,</u>
Item [56], U.S. PATENT DOCUMENTS, insert the following:

-- 5,537,585    7/1996    Blickenstaff et al. --.

<u>Column 6,</u>
Line 5, delete "," (comma) immediately after "diagnostic".

<u>Column 7,</u>
Line 26, delete "magnetooptical" and substitute -- magneto-optical -- in its place.

Signed and Sealed this

Eighteenth Day of March, 2003

JAMES E. ROGAN
*Director of the United States Patent and Trademark Office*